United States Patent [19]

Frigola-Constansa et al.

[11] Patent Number: 5,162,323

[45] Date of Patent: Nov. 10, 1992

[54] INHIBITION OF THE WITHDRAWAL SYNDROME

[75] Inventors: Jordi Frigola-Constansa; Juan Pares-Corominas, both of Barcelona, Spain

[73] Assignee: Laboratorios del Dr. Esteve, S.A., Barcelona, Spain

[21] Appl. No.: 615,257

[22] Filed: Nov. 19, 1990

[30] Foreign Application Priority Data

Nov. 22, 1989 [FR] France .................. 89 15316

[51] Int. Cl.$^5$ .................. A61K 31/505; C07D 403/14
[52] U.S. Cl. .................. 514/252; 544/295
[58] Field of Search .................. 544/295; 514/252

[56] References Cited

FOREIGN PATENT DOCUMENTS 0285008 10/1988 European Pat. Off. .
382637 8/1990 European Pat. Off. ............ 544/295

Primary Examiner—Patricia L. Morris
Attorney, Agent, or Firm—Dressler, Goldsmith, Shore, Sutker & Milnamow, Ltd.

[57] ABSTRACT

The present invention relates to the use of the derivatives of general formula I

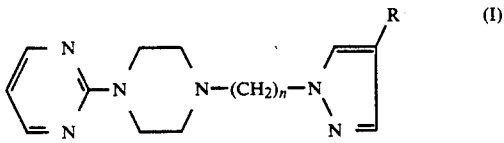

in which:

n can have the values 1 to 6, and

R represents a hydrogen atom, a halogen, a $C_1$ to $C_4$ lower alkyl radical, a nitro radical, a hydroxyl radical, an oxo radical, a $C_1$ to $C_4$ lower alkoxy radical, a cyano radical, a $C_1$ to $C_4$ lower alkyl carboxylate radical, an aryl or substituted aryl radical, or an amino or substituted amino radical of formula

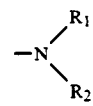

in which $R_1$ and $R_2$, which may be identical or different, represent a hydrogen atom, an alkyl radical, an aryl radical, an alkylcarboxy radical, an arylcarboxy radical, an alkylsulphonyl radical or an arylsulphonyl radical, the alkyl fragments of these radicals containing from 1 to 4 carbon atoms for the manufacture of medicinal products intended for the treatment of disorders associated with the withdrawal syndrome induced by the discontinuation of benzodiazepines such as diazepam, cocaine, alcohol and/or nicotine.

5 Claims, No Drawings

INHIBITION OF THE WITHDRAWAL SYNDROME

The present invention relates to the use of {ω-[4-(2-pyrimidinyl)-1-piperazinyl]alkyl}-1H-azole derivatives as well as their physiologically acceptable salts for the manufacture of medicinal products intended for the treatment of disorders associated with the withdrawal syndrome induced by the discontinuation of benzodiazepines, especially diazepam, cocaine, alcohol and/or nicotine.

Whereas all known anxiolytics have always proved incapable of inhibiting the withdrawal syndrome, it was found, altogether surprisingly, that some {ω-[4-(2-pyrimidinyl)-1-piperazinyl]alkyl}-1H-azole derivatives were very active for treating the disorders associated with such a syndrome.

The compounds recommended in the context of the present invention correspond to the general formula I

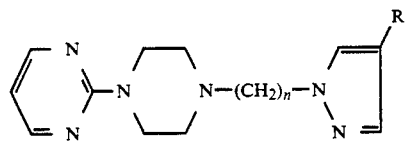

in which:
n can have the values 1 to 6, and
R represents a hydrogen atom, a halogen, a $C_1$ to $C_4$ lower alkyl radical, an heteroaryl radical, a sulpho radical or an N-substituted or N,N-disubstituted sulfamoyl radical, a nitro radical, a hydroxyl radical, an oxo radical, a $C_1$ to $C_4$ lower alkoxy radical, a cyano radical, a $C_1$ to $C_4$ lower alkyl carboxylate radical, an aryl or substituted aryl radical, or an amino or substituted amino radical of formula

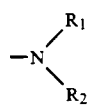

in which
$R_1$ and $R_2$, which may be identical or different, represent a hydrogen atom, an alkyl radical, an aryl radical, an alkylcarboxy radical, an arylcarboxy radical, an alkylsulphonyl radical or an arylsulphonyl radical, the alkyl fragments of these radicals containing from 1 to 4 carbon atoms.

These derivatives of general formula I may be prepared, according to the invention, according to any one of the following methods.

Method A

By the reaction of a compound of general formula II

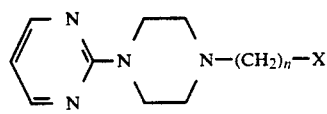

in which

X represents a halogen atom or a leaving group selected from tosyloxy or mesyloxy, with a compound of general formula III

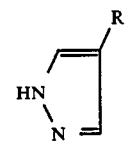

in which
R has the meanings stated above.

The reaction is performed in the presence of a suitable solvent, for example dimethyl sulphoxide, dimethylformamide, an alcohol, a hydrocarbon, aromatic or otherwise, an ether such as dioxane or diphenyl ether or a mixture of these solvents. This reaction is advantageously performed in the presence of a base such as alkali metal hydroxides, carbonates or bicarbonates, or alternatively a mixture of these bases. The most suitable temperatures vary between room temperature and the refluxing temperature of the solvent, and the reaction time is between 1 hour and 24 hours.

Method B

By the reduction of a compound of general formula I in which
R represents a nitro group.

Among the many reducing agents capable of being used for reducing a nitro group to an amino group, the following may be mentioned: catalytic hydrogenation using nickel, palladium or platinum as catalysts, zinc amalgam with hydrochloric acid, alkali metal borohydrides, and the like.

The reaction is performed in an alcohol such as methanol, ethanol or any of the propanols or butanols, or alternatively a mixture of an alcohol with water. The most suitable temperatures are between $-10°$ C. and that of refluxing of the solvent, and the reaction time is between 1 hour and 24 hours.

Method C

By the acylation of a compound of general formula I in which
R represents an amino group, with an acid halide or an anhydride.

The reaction is performed without a solvent or in the presence of a suitable solvent such as a hydrocarbon, a ketone or an ether, and in the presence of a base such as pyridine or the trialkylamines. The most suitable temperatures vary between $-10°$ C. and the boiling point of the solvent, and the reaction time is between 1 hour and 24 hours.

Method D

By the alkylative reduction of a compound of general formula I in which
R represents a nitro group, this alkylative reduction being carried out with an alkali metal borohydride in the presence of nickel II chloride and a compound which possesses a keto or aldehyde group. This reaction is performed in an alcohol or a mixture of alcohol and water. The most suitable temperatures vary between $-15°$ C. and that of refluxing of the solvent, and the reaction time is between a few minutes and 24 hours.

Method E

By the reaction of a compound of general formula IV

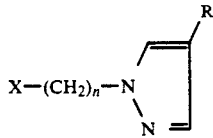

in which
X and n have the meanings stated above, with a compound of general formula V

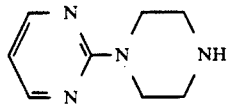

The examples which follow illustrate the preparation of a few derivatives falling within the scope of the present invention. A few modes of use will also be described.

Method A

Example 1

Preparation of
1-{4-[4-(2-pyrimidinyl)-1-piperazinyl]butyl}-1H-pyrazole

A mixture of 4 g (13.3 mmol) of 1-(2-pyrimidinyl)-4-(4-bromobutyl)piperazine, 1.02 g (15 mmol) of pyrazole and 2.76 g (20 mmol) of potassium carbonate in 50 ml of dimethylformamide is heated to reflux for 14 hours. The mixture is evaporated under vacuum, chloroform is added, the organic phase is washed with water, dried over sodium sulphate and evaporated under vacuum, and 3.5 g of an oil which is 1-{4-[4-(2-pyrimidinyl)-1-piperazinyl]butyl}-1H-pyrazole are obtained.

The compounds identified as Examples 1 to 9 are obtained by the same procedure, and the data for their identification are shown in Table I.

Method B

Example 10

Preparation of
4-amino-1-{4-[4-(2-pyrimidinyl)-1-piperazinyl]butyl}-1H-pyrazole 10.2 g (43.2 mmol) of nickel II chloride hexahydrate are added to a solution of 7.2 g (21 mmol) of 4nitro-1-{4-[4-(2-pyrimidinyl)-1-piperazinyl]butyl}-1H-pyrazole, Example no. 7, in 60 ml of ethanol, with vigorous stirring. The mixture is cooled in an ice bath and 10.2 g (81 mmol) of sodium borohydride are added slowly. The mixture is left stirring for 1 hour and, after 1 hour at room temperature, water is added, the mixture is evaporated under vacuum, the residue is acidified with concentrated hydrochloric acid and the mixture is filtered, alkalinised with ammonia solution and extracted with ethyl ether. 4.4 g of 4-amino-1-{4-[4-(2-pyrimidinyl)-1-piperazinyl]butyl}-1H-pyrazole are thereby obtained in liquid form.

The spectroscopic data for its identification are given in Table II.

Method C

Example 11

Preparation of
4-methylsulphonamido-1-{4-[4-(2-pyrimidinyl)-1-piperazinyl]butyl}-1H-pyrazole 1.8 g (16 mmol) of methanesulphonyl chloride are added slowly to a cooled solution of 4.4 g (14.6 mmol) of 4-amino-1-{4-[4-(2-pyrimidinyl)-1-piperazinyl]alkyl}-1H-pyrazole, Example 10, in 30 ml of pyridine. The mixture is left for 1 hour at 0° C., left at room temperature for 4 hours and poured into ice-cold water, the product is extracted with chloroform and 3.7 g of 4-methylsulphonamido-1-{4-[4-(2-pyrimidinyl)-1-piperazinyl]butyl}-1H-pyrazole are obtained, which compound may be crystallised in ethyl ether, with a melting point of 132° C.

The compounds identified as Examples 12 and 13 are obtained by the same method, and the data for their identification are shown in Table II.

Method D

Example 14

Preparation of
4-(2-butyl)amino-1-{4-[4-(2-pyrimidinyl)-1-piperazinyl]butyl}-1H-pyrazole 0.9 g (24 mmol) of sodium borohydride is added to a suspension, cooled to 0° C., of 2.8 g (12 mmol) of nickel dichloride hexahydrate in a solution of 2 g (6 mmol) of 4-nitro-1-{4-[4-(2-pyrimidinyl)-1-piperazinyl]butyl}-1H-pyrazole, Example 7, and 10 ml of methyl ethyl ketone in 50 ml of ethanol. This temperature is maintained for 30 minutes and allowed to rise to room temperature, stirring is continued for 2 hours, the mixture is evaporated under vacuum, the residue is taken up with ethyl acetate and 1.22 g of 4-(2-butyl))amino-1-{4-[4-(2-pyrimidinyl)-1-piperazinyl]butyl}-1H-pyrazole are obtained in liquid form.

The spectroscopic data for this product are shown in Table II.

TABLE I

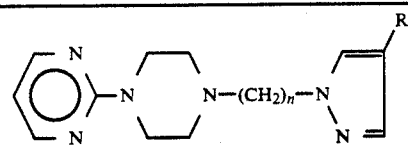

| Ex. | R | n | IR cm$^{-1}$ | $^1$H NMR, δ, CDCl$_3$, J=Hz |
|---|---|---|---|---|
| 1 | H | 4 | 2942, 2815, 1586, 1547, 983 | 1.50(m, 2H); 1.90(m, 2H); 2.40(m, 6H); 3.80(m, 4H); 4.12(t, 2H, J=6,9); 6.20 (t, 1H, J=1,6); 6.40(t, 1H, J=4.7); 7.42(dd, 2H, J=4.7; J'=1,6); 8.25(d.2H, J=4.7) |
| 2 | Me | 4 | 1590, 1550, 1500, 1360 1260, 980 | 1.52(m, 2H; 1.95(m, 2H); 2.05(s, 3H); 2.37(m.6H); 3.81(m, 4H); 4.05(t.2H, J=6.8); 6.41(t, 1H; J=4.7) 7.13(S, 1H); 7.27(s, 1H); 7.27(s, 1H); 8.25(d.2H, J=4.7) |
| 3 | NO$_2$ | 4 | 1584, 1524, 1480, 1444, 1406, 1359, 1305, 819 | 1.5(m, 2H); 1.93(m, 2H); 2.38(m, 6H); 3.76(m.4H); 4.15(t, 2H, J=6.7); 6.42 (t, 1H. J=4.7); 8.01(s, 1H) 8.12(s.1H); 8.24(d, 2H, J=4.7) |

TABLE I-continued

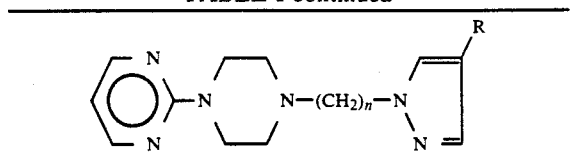

| Ex. | R | n | IR cm$^{-1}$ | $^1$H NMR, δ, CDCl$_3$, J=Hz |
|---|---|---|---|---|
| 4 | Cl | 4 | 2843, 1586, 1547, 1358, 983 | 1.52(m, 2H); 1.90(m, 2H); 2.43(m, 6H); 3.80(m.4H); 4.0(t, 2H, J=6.8); 6.44(t, 1H, J=4.7); 7.35(s, 1H) 7.39(s.1H); 8.25(d, 2H, J=4.7) |
| 5 | Et—OOC— | 4 | 1715, 1586, 1222, 983 | 1.34(t, 3H, J=7.1); 1.54 (m, 2H); 1.90(m, 2H); 2.46 (m, 6H); 3.81(m, 4H); 4.25 (m, 4H); 6.47(t, 1H, J=4.7); 7.90(s.2H); 8.29(d, 2H, J=4.7) |
| 6 | Br | 4 | 1586, 1547, 1360, 984 | 1.52(m, 2H); 1.89(m, 2H); 2.44(m.6H); 3.62(m.4H); 4.11(t, 2H, J=6.7); 6.46 (t, 1H, J=4.6); 7.42(s, 1H); 7.45(s, 1H); 8.29(d, 2H, J=4.6) |

TABLE I-continued

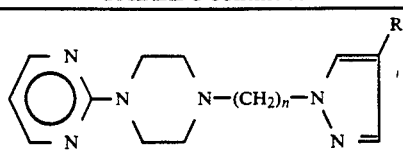

| Ex. | R | n | IR cm$^{-1}$ | $^1$H NMR, δ, CDCl$_3$, J=Hz |
|---|---|---|---|---|
| 7 | C≡N | 4 | 3076, 2231 1587, 1551 1258, 982 | 1.54(m, 2H); 1.96(m, 2H); 2.40(m.6H); 3.81(m.4H); 4.20(t, 2H, J=6.9); 6.48 (t, 1H, J=4.7); 7.80(s, 1H); 7.83(s, 1H); 8.29(d, 2H, J=4.7) |
| 8 | F | 4 | 2944, 1584 1546, 1507, 1359, 1260 983 | 1.45(m, 2H); 1.96(m, 2H); 2.36(m.6H); 3.77(m.4H); 4.0(t, 2H, J=6.9); 6.47 (t, 1H, J=4.7); 7.27(d, 1H, J=4.8); 8.29(d, 2H, J=4.8) |
| 9 | Me—O— | 4 | 2940, 1585, 1547, 1470, 1359, 1122, 983 | 1.54(m, 2H); 1.89(m, 2H); 2.42(m.6H); 3.77(m,7H); 4.06(m, 2H); 6.42(t, 1H, J=4.7); 7.02(s, 1H) 7.26 (s, 1H); 8.25(d, 2H, J=4.6) |

TABLE II

| Ex. | R | M.p. | n | IR | $^1$H NMR, δ, CDCl$_3$, J=Hz |
|---|---|---|---|---|---|
| 10 | H$_2$N— | oil | 4 | 1586, 1548, 1360, 984 | 1.50(m, 2H); 1.85(m, 2H) 2.43(m, 6H); 3.4(broad 2H); 3.8(m, 6H); 4.0(t, 24, J=6.4); 6.46(t, 1H, J=4.7); 6.98(s, 1H); 7.10(s, 1H); 8.27(d, 2H, J=4.7) |
| 11 | Me—SO$_2$—NH— | 132° C. | 4 | 1582, 1482, 1360, 1150, 983 | 1.58(m, 2H); 1.93(m, 2H) 2.45(m, 6H); 2.94(s, 3H); 3.8(m, 4H); 4.11(t, 2H, J=6.9); 6.45(t, 1H, J=4.7); 7.4(s, 1H); 7.5(s, 1H) 8.28(d, 2H, J=4.7) |
| 12 | Ph—CO—NH— | 134-6° C. | 4 | 1646, 1586, 1542, 1369 | 1.55(m, 2H); 1.79(s, 3H); 1.88(m, 2H); 2.42(m, 6H); 3.80(m, 4H); 4.13(t, 2H, J=6.8); 6.51(t, 1H, J=4.7); 7.49(m, 4H); 7.83(m, 2H); 8.0(s, 1H); 8.11(s.1H); 8.28(d, 2H, J=4.7) |
| 13 | Me—CO—NH— | 80-2° C. | 4 | 1650, 1586, 1454, 1364, 1261, 983 | 1.50(m, 2H); 1.88(m, 2H); 2.11(s, 3H); 2.43(m, 6H); 3.79(m, 4H); 4.08(t, 2H, J=6.8); 6.47(t, 1H, J=4.7); 7.36(s, 1H) 7.93(s, 1H); 8.28(d, 2H, J=4.6); 9.25(s, 1H) |
| 14 | Me\\CH—NH—/Et | Oil | | 2960, 1585, 1547, 1359, 1260 983 | 1.00(t, 3H, J=7.0); 1.19 (d, 3H, J—6.3); 1.6(m, 4H); 1.90(m, 2H); 2.50(m, 6H); 3.0(m, 3H); 3.9(m, 4H); 4.1(t, 2H, J=6.8); 6.52 (t, 1H, J=4.7); 6.99(s.1H); 7.17(s, 1H); 3.37(d, 2H, J=4.7) |
| 15 | Me—O—⟨C$_6$H$_4$⟩— | 79-82° C. | 4 | 2390, 1589, 1545, 1495, 1360, 1247, 983, 835, 799 | 1.62(m, 2H); 1.88(m, 2H); 2,45(m, 6H); 3.81(m, 7H); 4.16(t, 2H, J=6,8); 6.46(t, 1H, J=4,7); 6.9(d, 2H, J=4,4); 7.4(d, 2H, J=4,4); 7.55(s, 1H); 7.7(s, 1H); 8.28(d, 2H, J=2,4) |

TABLE II-continued

| # | Structure | mp | | IR | NMR |
|---|---|---|---|---|---|
| 16 | 4-Cl-C6H4- | 108–110° C. | 4 | 2946, 1586, 1549, 1485, 1395, 1257, 982, 951, 830 | 1.6(m, 2H); 1.9(m, 2H); 2.46(m, 6H); 3.8(m, 4H); 4.16(t, 2H, J=6,8); 6.4(t, 1H, J=4,7); 7.36(d, 4H, J=1,3); 7.7(d, 2H, J=6,2); 8.28(d, 2H, J=2,3) |
| 17 | —N(pyrrolyl) | Oil | 4 | 2943, 1586, 1487, 1359, 1260, 984, 726 | 1.55(m, 2H); 1.80(m, 2H); 2.45(m, 6H); 3.81(t, 4H, J=5); 4.12(t, 2H, J=7); 6.25(2H, t, J=2); 6.44(1H, t, J=4,7); 6.84(m, 2H); 7.5(d, 2H, J=5); 8.27(d, 2H, J=4,7) |
| 18 | C6H5- | 39–42° C. | 4 | 2942, 1585, 1493, 1446, 1359, 1258, 983, 760 | 1.6(m, 2H); 1.9(m, 2H); 2.5(m, 4H); 3.8(m, 6H); 4.2(t, 2H, J=6,8); 6.7(t, 1H, J=4,7); 7.2–7.7(compl. abs. 5H); 8.0(s, 1H); 8.2(s, 1H); 8.4(d, 2H, J=2,3) |
| 19 | C6H5-SO2-NH- | 92–95° C. | 4 | 2931, 1584, 1548, 1490, 1358, 1167, 983 | 1.45(m, 2H); 1.85(m, 2H); 2.40(m, 6H); 3.80(m, 4H); 4.0(t, 2H, J=6,7); 6.47(t, 1H, J=4,6); 7.0(s, 1H); 7.5(m, 6H); 8.3(d, 2H, J=4,6) |
| 20 | Me-C6H4-SO2-NH | 108–110° C. | 4 | 2943, 1585, 1548, 1446, 1360, 1161, 984 | 1.5(m, 2H); 1.85(m, 2H); 2.28(m, 9H); 3.8(m, 4H); 4.0(m, 2H); 6.45 t, 1H, J=4,7); 7–7.65(m, 6H); 8.27(d, 2H, J=4,7) |
| 21 | n-Bu—SO2—NH— | Oil | 4 | 2941, 1586, 1548, 1448, 1360, 1146, 984, 755 | 0.91(t, 3H, J=6,8); 1,45(m, 4H); 1.85(m, 4H); 2.40(m, 6H); 3.0(m, 2H); 3.80(m, 4H); 4.11(t, 2H, J=6,5); 6.5(t, 1H, J=4,7); 7.4(m, 2H); 7.5(s, 1H); 8.3(d, 2H, J=4,7) |
| 22 | n-Pr—SO2—NH— | Oil | 4 | 2940, 1586, 1548, 1447, 1360, 1146, 984, 755 | 1.0(t, 3H, J=7,1); 1.55(m, 2H); 1.9(m, 4H); 2.45(m, 6H); 3.0(t, 2H, J=7,4); 3.8(m, 4H); 4.1(t, 2H, J=6,4); 6.46(t, 1H, J=4,7); 7.35(m, 2H); 7.5(s, 1H); 8.3(d, 2H, J=4,7) |
| 23 | Et—SO2—NH— | Oil | 4 | 2943, 1586, 1548, 1447, 1360, 1146, 984, 754 | 1.36(m, 5H); 1.9(m, 2H); 2.45(m, 6H); 3.0(m, 2H); 3.6(m, 4H); 4.1(t, 2H, J=6,4); 6.45(t, 1H, J=4,7); 7.39(s, 1H); 7.51(s, 1H); 8.3(d, 2H, J=4,7) |
| 24 | —SO2—N—Me2 | 100–102° C. | 4 | 3135, 2943, 1586, 1512, 1357, 1328, 1156, 982, 728 | 1.6(m, 2H); 1.9(m, 2H); 2.3–2.7(compl. abs. 13H); 3.8(m, 4H); 4.2(t, 2H, J=6,8); 6.4(t, 1H, J=4,7); 7.75(d, 1H, J=4,4); 8.28(d, 2H, J=2,4) |
| 25 | —SO3—H | 230–235° C. (dec.) | 4 | 3330, 1590, 1556, 1449, 1220 | 1.95(m, 2H); 3.3(m, 6H); 4.0(s, 5H); 4.27(t, 2H, J=6,1); 6.8(t, 1H, J=4,8); 7.8(s, 1H); 8.0(s, 1H); 8.43(d, 2H, J=2,4) |

TABLE II-continued 1178,
1049,
971,
656

[Structure: pyrimidine-N-piperazine-N-(CH$_2$)$_n$-N-pyrazole(R) · X]

| Ex. | R | X | P.F. | n | IR cm$^{-1}$ |
|---|---|---|---|---|---|
| 26 | Cl | 1HCl | 156–158° C. | 4 | 3490, 1592, 1556, 1481, 1438, 1386, 970 |
| 27 | Cl | 2HCl.H$_2$O | 194–197.5° C. | 4 | 3429, 2688, 1636, 1620, 1346, 1218, 971 |

Study of the anxiolytic or anxiogenic activity in mice

The light box/dark box test described by B. Costall et al. (J. Phar. Pharmacol., 1988, 40: 494–500) is used. The mouse is placed in the light area of a box divided into two compartments, one brightly lit, the light box, and the other one poorly lit, the dark box.

1) The number of times the mouse rears on its hind legs in each compartment is counted during 5 minutes (see column 1 of the table below).
2) The activity in each compartment is given by counting the number of crossings over the squares which make up the divisions of each compartment (see column 2 of the table below).
3) The time spent in the dark box is measured during the 5 minutes of counting (see column 3 of the table below).
4) The initial latency, that is to the say the time elapsing between placing the animal in the light box at the beginning of the trial and its entry into the dark box, is determined (see column 4 of the table below).

The anxiolytic or anxiogenic behaviour of the mice is determined during the different treatment periods, always comparing it with that of a group of control animals which have undergone no treatment.

Treatments and experimental design

1) Dependence on a particular treatment (diazepam, cocaine, alcohol or nicotine) in the form of daily administration for a period of 7 or 14 days. This treatment produces an anxiolytic response (activity and time spent in the light box increase).

| | Dosages: |
|---|---|
| Diazepam: | 10 mg/kg i.p. twice daily for 7 days. |
| Cocaine: | 1 mg/kg i.p. for 14 days. |
| Alcohol: | administered at a concentration of 8% weight/volume in the drinking water for 14 days. |
| Nicotine: | 0.1 mg/kg i.p. twice daily for 14 days. |

2) Discontinuation of the treatment, producing in the course of 24 hours a withdrawal syndrome which manifests itself as an anxiogenic response (increases activity and time in the dark box).
3) Various other groups receive, in addition to diazepam, cocaine, alcohol or nicotine, a concomitant treatment with products which are the subject of the present invention and, by way of comparison, with buspirone or ipsapirone. Treatment with diazepam, cocaine, alcohol or nicotine is withdrawn from these groups also, and the response after 24 hours is likewise observed.

The products described and the doses tested were:
4-chloro-1-{4-[4-(2-pyrimidinyl)-1-piperazinyl]butyl}-1H-pyrazole
(Example 4): 0.5 mg/kg i.p. twice daily.
1-{4-[4-(2-pyrimidinyl)-1-piperazinyl]butyl}-1H-pyrazole
(Example 1): 0.5 mg/kg i.p. twice daily.
4-Methylsulphonamido-1-{4-[4-(2-pyrimidinyl)-1-piperazinyl]butyl}-1H-pyrazole
(Example 11): 1 mg/kg i.p. twice daily (against diazepam, alcohol and nicotine) and 0.5 mg/kg i.p. twice daily (against cocaine).

The results observed have been recorded in the tables below.

The responses obtained with the products which are the subjects of the present invention were as follows:

The derivatives of Examples 1 and 4 inhibit the withdrawal syndrome, which manifests itself as an anxiogenic response, induced by diazepam, cocaine, alcohol and nicotine, and in addition they maintain a significant anxiolytic response when the administration of diazepam, cocaine, alcohol or nicotine is discontinued.

The derivative of Example 11 inhibits the withdrawal syndrome, which manifests itself as an anxiogenic response, induced by diazepam, alcohol and nicotine, and in addition it maintains a significant anxiolytic response when the administration of diazepam and alcohol is discontinued.

Buspirone maintains the withdrawal syndrome, which manifests itself in an anxiogenic response, induced by diazepam and cocaine. However, when treatment with alcohol and nicotine is discontinued, a withdrawal syndrome, i.e. anxiogenesis, no longer persists. Buspirone significantly inhibits only a few parameters of anxiogenic response after discontinuation of alcohol treatment.

Ipsapirone maintains the withdrawal syndrome, which manifests itself in an anxiogenic response, induced by diazepam, cocaine and nicotine. Ipsapirone inhibits the withdrawal syndrome, which manifests itself in the form of an anxiogenic response, induced by alcohol.

EFFECT OF LONG TERM DIAZEPAM TREATMENT AND DISCONTINUATION. INHIBITION OF THE WITHDRAWAL SYNDROME WITH THE PRODUCTS CORRESPONDING TO EXAMPLES 1, 4 and 11.

| TREATMENT | REARING SCORE IN 5 MIN. L-D | ACTIVITY SCORE IN 5 MIN. L-D | TIME IN BOX D | | Lat. L-D |
|---|---|---|---|---|---|
| Control | 28 | 92 | 38 | 80 | 58 | 13 |
| Diazepam | 70* | 25* | 73* | 24* | 25* | 27* |
| Diaz. + discontin. 24 h | 5+ | 98+ | 9+ | 100+ | 75+ | 9+ |
| Diaz. + discontin. 24 h + Ex. 1 | 80·* | 22·* | 82·* | 25·* | 30·* | 30·* |
| Diaz. + discontin. 24 h + Ex. 4 | 82·* | 24·* | 100·* | 28·* | 25·* | 38·* |
| Diaz. + discontin. 24 h + Ex. 11 | 70·* | 25·* | 72·* | 27·* | 25·* | 22·* |
| Diaz. + discontin. 24 h + buspirone | 9+ | 88+ | 12+ | 100+ | 72+ | 2+ |
| Diaz. + discontin. 24 h + ipsapirone | 15+ | 82+ | 17+ | 88+ | 90+ | 8+ |

EFFECT OF LONG TERM COCAINE TREATMENT AND DISCONTINUATION. INHIBITION OF THE WITHDRAWAL SYNDROME WITH THE PRODUCTS CORRESPONDING TO EXAMPLES 1, 4 and 11.

| TREATMENT | REARING | ACTIVITY | | | BOX | Lat. |
|---|---|---|---|---|---|---|
| Control | 23 | 71 | 32 | 80 | 58 | 10 |
| Cocaine | 60* | 38* | 68* | 30* | 30* | 18* |
| Coca. + discontin. 24 h | 8+ | 102+ | 10+ | 105+ | 75+ | 3+ |
| Coca. + discontin. 24 h + Ex. 1 | 60·* | 40·* | 65·* | 20·* | 30·* | 16·* |
| Coca. + discontin. 24 h + Ex. 4 | 80·* | 20·* | 85·* | 25·* | 25·* | 33·* |
| Coca. + discontin. 24 h + Ex. 11 | 5+ | 90+ | 18+ | 100+ | 70+ | 4+ |
| Coca. + discontin. 24 h + buspirone | 10+ | 98+ | 18+ | 90+ | 70+ | 2+ |
| Coca. + discontin. 24 h + ipsapirone | 11+ | 89+ | 18+ | 85+ | 62+ | 8+ |

EFFECT OF LONG TERM ALCOHOL TREATMENT AND DISCONTINUATION. INHIBITION OF THE WITHDRAWAL SYNDROME WITH THE PRODUCTS CORRESPONDING TO EXAMPLES 1, 4 and 11.

| TREATMENT | REARING | ACTIVITY | | | BOX | Lat. |
|---|---|---|---|---|---|---|
| Control | 23 | 72 | 37 | 76 | 58 | 13 |
| Alcohol | 72* | 22* | 80* | 28* | 28* | 28* |
| Alcohol + discontin. 24 h | 8+ | 98+ | 10+ | 108+ | 70+ | 4+ |
| Alcohol + discontin. 24 h + Ex. 1 | 85·* | 21·* | 85·* | 28·* | 25·* | 32·* |
| Alcohol + discontin. 24 h + Ex. 4 | 85·* | 20·* | 92·* | 18·* | 25·* | 40·* |
| Alcohol + discontin. 24 h + Ex. 11 | 55·* | 35·* | 60·* | 40·* | 28·* | 19·* |
| Alcohol + discontin. 24 h + buspirone | 18· | 80· | 15· | 75· | 62· | 7· |
| Alcohol + discontin. 24 h + ipsapirone | 21· | 75· | 36· | 80· | 35· | 10· |

EFFECT OF LONG TERM NICOTINE TREATMENT AND DISCONTINUATION. INHIBITION OF THE WITHDRAWAL SYNDROME WITH THE PRODUCTS CORRESPONDING TO EXAMPLES 1, 4 and 11.

| TREATMENT | REARING SCORE IN 5 MIN. L-D | ACTIVITY SCORE IN 5 MIN. L-D | TIME IN BOX D | | Lat. L-D |
|---|---|---|---|---|---|---|
| Control | 22 | 70 | 30 | 75 | 57 | 12 |
| Nicotine | 66* | 23* | 70* | 25* | 25* | 26* |
| Nic. + discontin. 24 h | 10+ | 96+ | 12+ | 105+ | 70+ | 4+ |
| Nic. + discontin. 24 h + Ex. 1 | 75·* | 22·* | 65·* | 20·* | 23·* | 28·* |
| Nic. + discontin. 24 h + Ex. 4 | 78·* | 20·* | 90·* | 22·* | 23·* | 42·* |
| Nic. + discontin. 24 h + Ex. 11 | 28· | 68· | 40· | 68· | 30· | 15· |
| Nic. + discontin. 24 h + buspirone | 12 | 80 | 20 | 85 | 65 | 8 |
| Nic. + discontin. 24 h + ipsapirone | 9+ | 84+ | 18+ | 98+ | 70+ | 3+ |

*: $p\ 0.001$ (anxiolysis)
+: $p\ 0.001$ (anxiogenesis)
·: $p\ 0.001$ (reversal of the anxiogenesis)
L-D: Light-Dark The derivatives of general formula I according to the invention are hence useful as active substances of medicinal products intended for the treatment of disorders associated with the withdrawal syndrome which manifests itself especially in the form of an anxiogenic response, induced by the abrupt discontinuation of a prolonged treatment with benzodiazepines such as diazepam, or cocaine, or a prolonged intake of alcohol and/or nicotine.

In human therapy, the administration dose is naturally dependent on the severity of the syndrome.

It will generally be between approximately 5 and approximately 100 mg/day.

The derivatives of the invention will, for example, be administered in the form of tablets, solutions, suspensions or alternatively gelatin capsules.

Two particular pharmaceutical dosage forms are given below by way of examples.

| Example of formula per tablet | |
|---|---|
| Compound 1 | 5 mg |
| Lactose | 60 mg |
| Microcrystalline cellulose | 25 mg |
| Povidone | 5 mg |
| Pregelatinised starch | 3 mg |
| Colloidal silica | 1 mg |
| Magnesium stearate | 1 mg |
| Tablet weight | 100 mg |
| Example of formula per gelatin capsule | |
| Compound 4 | 10 mg |
| Polyoxyethylenated glycerol | 135 mg |
| Glyceryl benhenate | 5 mg |
| Excipient: soft gelatine q.s. | 150 mg |

We claim:

1. Method of treating a patient for disorders associated with the withdrawal syndrome associated with the discontinuation of at least one drug of the group consisting of benzodiazepines, cocaine, alcohol and nicotine which comprises administering to said patient, in an amount effective to ameliorate said withdrawal syndrome, a compound of the formula I

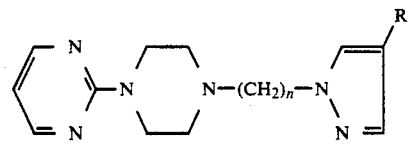

in which:
n can have the values 1 to 6, and
R represents a hydrogen atom, a halogen, a $C_1$ to $C_4$ lower alkyl radical, a pyrrolyl radical, a sulpho radical or an N,N-dimethylsulphamoyl radical, a nitro radical, a hydroxy radical, an oxo radical, a $C_1$ to $C_4$ lower alkoxy radical, a cyano radical, a $C_1$ to $C_4$ lower alkyl carboxylate radical, a methoxyphenyl radical, a chlorophenyl radical, or an amino or substituted amino radical of formula

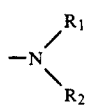

in which
$R_1$ and $R_2$, which may be identical or different, represent a hydrogen atom, an alkyl radical, an alkanoyl radical, a benzyl radical, an alkylsulphonyl radical, a phenylsulphonyl radical, or an alkylbenzene sulphonyl radical, the alkyl fragments of these radicals containing from 1 to 4 carbon atoms, and their therapeutically acceptable salts.

2. The method according to claim 1, characterized in that the compound formula I is selected from the group consisting of:
1—1-{4-[4-(2-pyrimidinyl)-1-piperazinyl]butyl}-1H-pyrazole,
2—4-methyl-1-1-{4-[4-(2-pyrimidinyl)-1-piperazinyl]butyl}-1H-pyrazole,
3—4-nitro-1-{4-[4-(2-pyrimidinyl)-1-piperazinyl]butyl}-1H-pyrazole,
4—4-chloro-1-{4-[4-(2-pyrimidinyl)-1-piperazinyl]butyl}-1H-pyrazole,
5—4-ethoxycarbonyl-1-{4-[4-(2-pyrimidinyl)-1-piperazinyl]butyl}-1H-pyrazole,
6—4-bromo-1-{4-[4-(2-pyrimidinyl)-1-piperazinyl]butyl}-1H-pyrazole,
7—4-cyano-1-{4-[4-(2-pyrimidinyl)-1-piperazinyl]butyl}-1H-pyrazole,
8—4-fluoro-1-{4-[4-(2-pyrimidinyl)-1-piperazinyl]butyl}-1H-pyrazole,
9—4-methoxy-1-{4-[4-(2-pyrimidinyl)-1-piperazinyl]butyl}-1H-pyrazole,
10—4-amino-1-{4-[4-(2-pyrimidinyl)-1-piperazinyl]butyl}-1H-pyrazole,
11—4-methylsulphonamido-1-{4-[4-(2-pyrimidinyl)-1-piperazinyl]butyl}-1H-pyrazole,
12—4-benzamido-1-{4-[4-(2-pyrimidinyl)-1-piperazinyl]butyl}-1H-pyrazole,
13—4-acetamido-1-{4-[4-(2-pyrimidinyl)-1-piperazinyl]butyl}-1H-pyrazole,
14—4-(2-butyl)amino-1-{4-[4-(2-pyrimidinyl)-1-piperazinyl]butyl}-1H-pyrazole,
15—4-(4-methoxyphenyl)-1-{4-[4-(2-pyrimidinyl)-1-piperazinyl]butyl}-1H-pyrazole,
16—4-(4-chlorophenyl)-1-{4-[4-(2-pyrimidinyl)-1-piperazinyl]butyl}-1H-pyrazole,
17—4-(1-pyrrolyl)-1-{4-[4-(2-pyrimidinyl)-1-piperazinyl]butyl}-1H-pyrazole,
18—4-phenyl-1-{4-[4-(2-pyrimidinyl)-1-piperazinyl]butyl}-1H-pyrazole,
19—4-phenylsulphonamido-1-{4-[4-(2-pyrimidinyl)-1-piperazinyl]butyl}-1H-pyrazole,
20—4-(4-methylbenzenesulphonamido)-1-{4-[4-(2-pyrimidinyl)-1-piperazinyl]butyl}-1H-pyrazole,
21—4-butylsulphonamido-1-{4-[4-(2-pyrimidinyl)-1-piperazinyl]butyl}-1H-pyrazole,
22—4-propylsulphonamido-1-{4-[4-(2-pyrimidinyl)-1-piperazinyl]butyl}-1H-pyrazole,
23—4-ethylsulphonamido-1-{4-[4-(2-pyrimidinyl)-1-piperazinyl]butyl}-1H-pyrazole,
24—4-(N,N-dimethylsulphamoyl)-1-{4-[4-(2-pyrimidinyl)-1-piperazinyl]butyl}-1H-pyrazole,
25—4-sulphonyl-1-{4-[4-(2-pyrimidinyl)-1-piperazinyl]butyl}-1H-pyrazole,
26—4-chloro-1-{4-[4-(2-pyrimidinyl)-1-piperazinyl]butyl}-1H-pyrazole hydrochloride,
27—4-chloro-1-{4-[4-(2-pyrimidinyl)-1-piperazinyl]butyl}-1H-pyrazole dihydrochloride.

3. The method of claim 1 wherein R in said formula I is a hydrogen atom.

4. The method of claim 1 wherein R in said formula I represents a halogen, a $C_1$ to $C_4$ lower alkyl radical, a nitro radical, a hydroxy radical, a $C_1$ to $C_4$ lower alkoxy radical, a cyano radical or a $C_1$ to $C_4$ lower alkyl carboxylate radical.

5. The method of claim 1 wherein R in said formula I is an amino or substituted amino radical of the formula $$N\begin{matrix}R_1\\R_2\end{matrix}$$

in which $R_1$ and $R_2$, which may be identical or different represent the same atom or radicals specified in claim 1.

* * * * *